United States Patent [19]

Ring

[11] 3,983,868
[45] Oct. 5, 1976

[54] INSERTER FOR LOW DENSITY TAMPONS

[75] Inventor: David F. Ring, Neenah, Wis.

[73] Assignee: Kimberly-Clark Corporation, Neenah, Wis.

[22] Filed: Feb. 13, 1976

[21] Appl. No.: 657,966

[52] U.S. Cl............................... 128/263; 128/285
[51] Int. Cl.² ........................................ A61F 15/00
[58] Field of Search........... 128/2 W, 263, 285, 130, 128/270, 242

[56] References Cited
UNITED STATES PATENTS

| | | | |
|---|---|---|---|
| 2,733,714 | 2/1956 | Haas | 128/263 |
| 3,831,605 | 8/1974 | Fournier | 128/263 |
| 3,857,395 | 12/1974 | Johnson et al. | 128/263 |

*Primary Examiner*—Aldrich F. Medbery
*Attorney, Agent, or Firm*—Daniel J. Hanlon, Jr.; William D. Herrick; Raymond J. Miller

[57] ABSTRACT

An inserter for low density tampons adapted to provide sufficient internal rigidity to the tampon to permit insertion, and to radially or laterally spread the tampon after insertion. The inserter has two telescopically associated tubular members. The outer member has an internal central shaft over which the tampon is draped and which provides the insertion end of the tampon with its necessary rigidity while also serving as a guide rail for the inner member. The wall of the outer member encloses and retains the trailing end portion of the draped tampon during insertion. The inner member is disposed in slidable relationship with the inner walls and with the central shaft of the outer member and is used to expel the tampon from the outer tube and to spread the trailing end portion after expulsion while the forward end of the tampon is held against movement.

14 Claims, 14 Drawing Figures

INSERTER FOR LOW DENSITY TAMPONS

BACKGROUND OF THE INVENTION

It is known that absorbent tampons made of soft deformable materials such as uncompressed batts of cotton fibers, rayon fibers, hydrophilic polyurethane foams, and the like, provide a much higher useful capacity for menstrual exudate than highly compressed materials now in common use. Further, if they are properly deployed at the time of insertion they also provide a more efficient protection against early leakage.

These favorable characteristics are attributed to the fact that low density absorbent materials in their initial relatively uncompressed state are already in the best condition for the most efficient use of their absorptive capabilities, and do not need to be wetted to expand and arrive at this improved state as is required by the traditional compressed tampon structures. Further, the soft deformable condition of these uncompressed materials permits them to confrom readily to the irregular configurations of the vaginal walls and thus effectively block leakage at an early stage after insertion.

The main problem in utilizing the high absorbency and leakage blocking capabilities of such uncompressed low density tampons is to find a means for efficiently delivering the soft material to a suitable position within the vaginal cavity, i.e., to insert a soft tampon to the proper depth in the vagina, and also to spread the tampon laterally or radially at the time of delivery.

The present invention is directed to a tampon inserter which provides such delivery means.

SUMMARY OF THE INVENTION

The inserter of this invention is comprised of a pair of telescopically associated outer and inner tubular members. The outer tube is provided with an internal axially-disposed central shaft suspended inside of the tube by support means associated with the inner wall of the outer tube and extending from the area of support through a portion of the outer tube and beyond the other end for a predetermined distance. The inner tubular member is longer than the outer tube and preferably has a reduced diameter portion at its forward end adapted to encircle and embrace the central shaft of the outer tube in slidable relationship with the shaft, while helping to spread the trailing ends of the tampon by a wedging action as the ends are expelled. The cylindrical wall of the inner tube is also provided with at least one elongated longitudinal slot to accommodate the support means of the shaft and to permit longitudinal movement between the two tubes. When the inserter is assembled and in operative association with a tampon, the tampon is draped over the leading end of the central shaft with the trailing end portions of the tampon tucked inside the outer tube circumferentially of the shaft. The walls of the inner tube are slidably associated with the walls of the outer tube and the inner tube has its reduced diameter end slidably engaged with the shaft and in contact with the tucked-in ends of the tampon. The tampon has a withdrawal string attached to its central forward end. In the preferred assembly this string extends down the shaft and out of the rear end of the outer tube. The free end of the string is threaded through the slot of the inner tube in a position where it can be held against the rear end of the outer tube by the fingers of the user during insertion. In another embodiment the outer tube may also be provided with a suitable aperture or slot to accommodate the withdrawal string.

The assembly is then inserted into the vagina until the soft tampon, while rigidly supported by the central shaft, is located at the desired depth. While the string is held against the rear end of the outer tube the inner tube is pushed forward to expel the trailing ends of the tampon from the outer tube. Since the string is attached to the forward end of the tampon, it immobilizes that end of the tampon while the trailing end of the tampon is expelled, whereupon the middle sections of the tampon are caused to buckle outward to break any temporary compression set which may have occurred as a result of compact packaging. The movement of the forward end of the inner tube into the interior of the tampon during the expelling action also spreads the free ends of the tampon laterally and/or radially as they leave the outer tube to aid in preventing leakage along the vaginal walls.

The outer tube element may be of unitary construction wherein the shaft is directly suspended from the inner wall of the tube, or the shaft and support means may comprise a separate piece which snaps in place inside of a separate outer tube.

The inserter elements are preferably made of a smooth flexible plastic such as low or high density polyethylene or polypropylene, but other materials such as paperboard, other cellulosic materials, or water-soluble plastics may also be employed if flushability is desired.

Other embodiments and advantages of the invention will become apparent by reference to the accompanying drawings and detailed description.

DETAILED DESCRIPTION OF THE DRAWINGS AND PREFERRED EMBODIMENTS OF THE INVENTION

Figure 1:
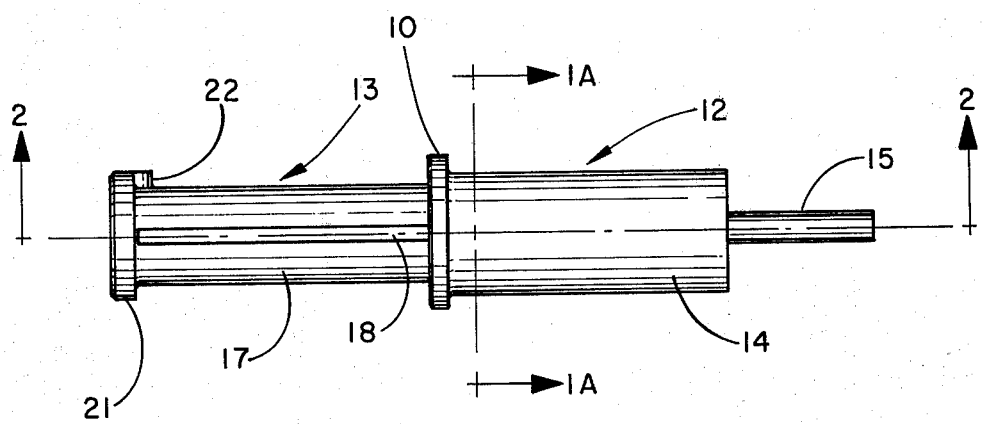
FIG. 1 is a side view of one embodiment of the tampon inserter of this invention.
Figure 2:
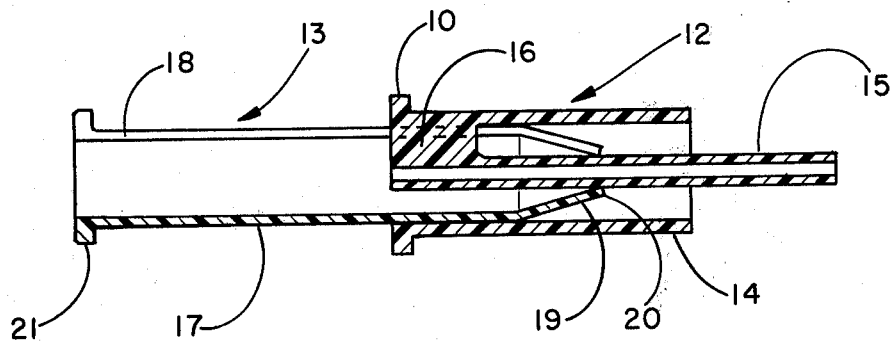
FIG. 2 is a longitudinal section taken through lines 2—2 of FIG. 1.

In FIGS. 1 through 2 of the drawings there are shown several views of one preferred embodiment of the tampon inserter of this invention. As shown therein the inserter is comprised of an outer tubular member 12 and an inner tubular member 13 in telescopic association. Outer tubular member 12 is comprised of a cylinder 14 open at both ends and has an elongated central shaft 15 axially disposed therein. Central shaft 15 is held in its axial disposition within outer cylinder 14 by a support means 16 comprised of a narrow flat vane extending from the rear portion of the inner wall of cylinder 14 to the rear end of shaft 15 as shown. Shaft 15 extends from the support area at one end of cylinder 14 completely through and beyond the outer end of the cylinder a substantial distance. The rear portion of the outer tubular element is also preferably provided with a raised peripheral ring 10 or a similar gripping aid.

Inner tubular element 13 is also comprised of a cylindrical member 17 in telescopic association with outer element 12. Cylinder 17 is provided with an elongate slot 18 which is open at its forward end to accommodate supporting vane 16 and to permit longitudinal slidable movement between inner element 13 and outer element 12. The forward end 20 of inner element 13 is of reduced diameter, preferably tapered as shown at 19, to embrace and be in slidable engagement with shaft 15. The extreme leading portion of forward end 20 may also be beveled to provide a sharper edge if desired. The rear end of inner element 13 is also preferably provided with a raised peripheral ring 21 and a small stud-like stop means 22. The stop means is provided to maintain the facing surface rings 10 and 22 from coming into full contact where the tubular elements are fully telescoped together as shown in FIG. 6 to provide a space through which withdrawal string 24 may escape after tampon placement while also insuring against skin or hair entrapment during use.

Figure 3:
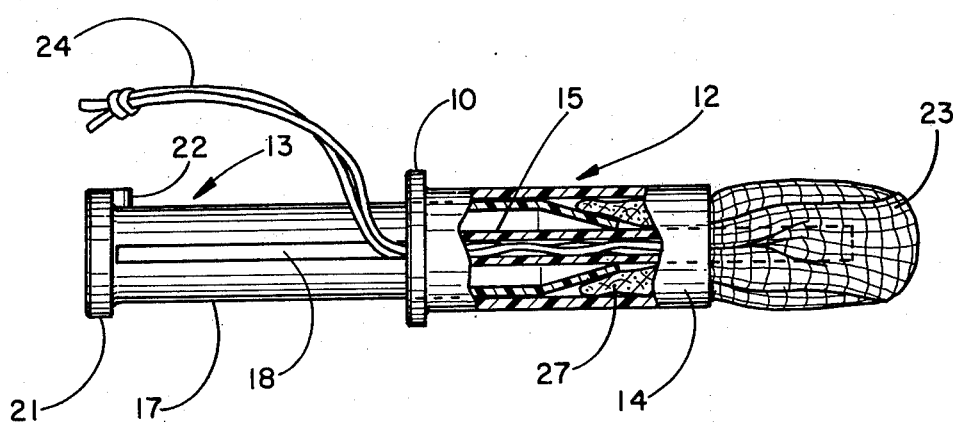
FIG. 3 is a side view, with portions partially cut away, of the inserter of FIG. 1 having a tampon disposed therein.

In FIG. 3, the FIG. 1 inserter of this invention is shown in combination with a soft deformable low density tampon. The tampon in this instance is comprised of flat strips of thin flexible absorbent sheet material with each strip enclosed in pervious wrapper. The strips cross each other at their mid-points and have a withdrawal string secured at the midpoint crossing, i.e. at the approximate geometric center of the tampon. The string is threaded through the center of hollow shaft 15 with its free end extending out of the rear end of the shaft and through slot 18 of the inner element. The tampon is draped over the forward end of the shaft and the free ends 27 of the tampon are stuffed into the open end of cylinder 14 to be confined between the walls of cylinder 14 and shaft 15. The thus-assembled tampon and inserter are now ready for insertion.

Figure 4:
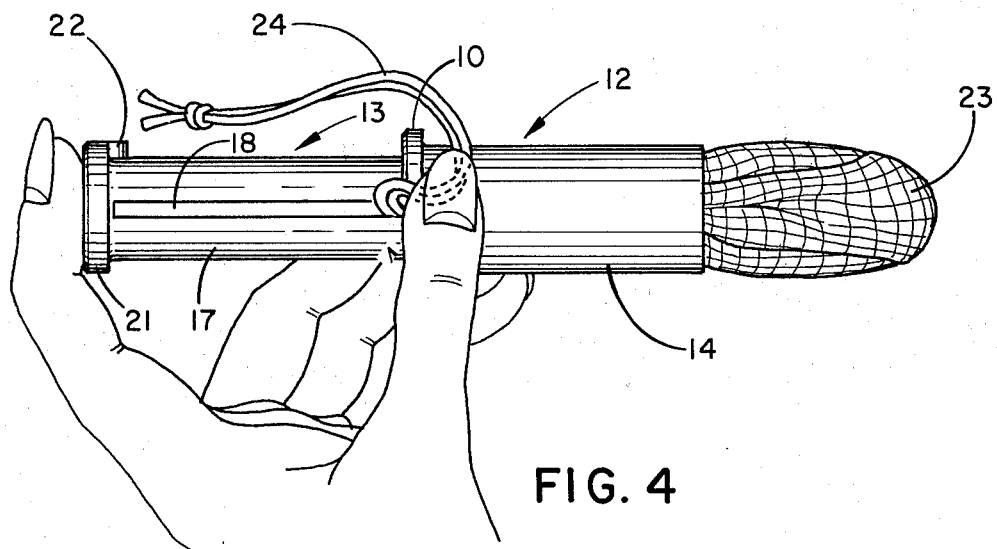
FIG. 4 is a side view similar to FIG. 3 showing how the inserter and tampon are held ready for insertion.
Figure 5:
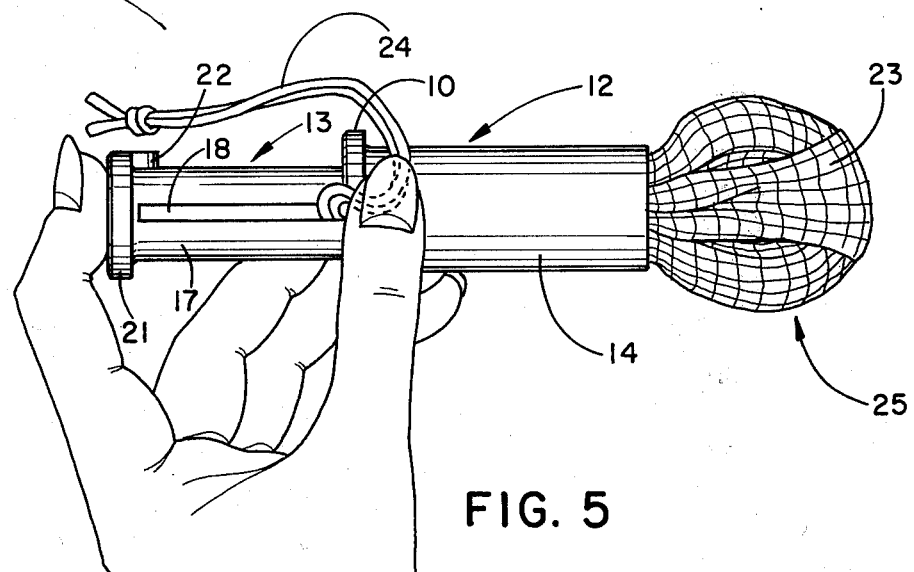
FIG. 5 is a side view similar to FIG. 4 showing the tampon partially expelled.
Figure 6:
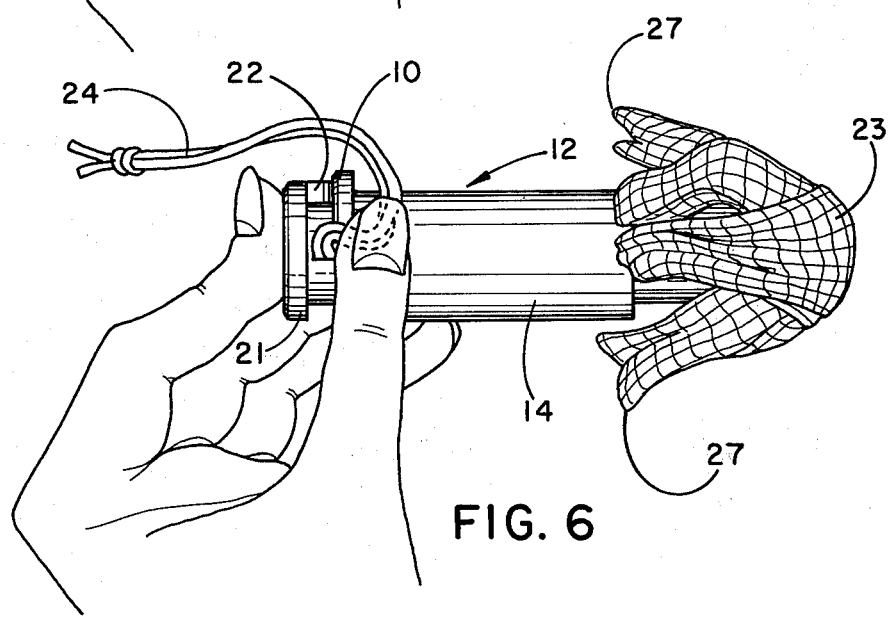
FIG. 6 is a side view similar to FIG. 4 showing the tampon fully expelled.

FIGS. 4 through 6 illustrate the various configurations the inserter-tampon combination takes as it is being inserted by the user. Preparatory to insertion, the outer element 12 is preferably grasped at ring 10 by the fingers with string 24 held firmly against movement by the thumb or middle finger. The tampon and outer element are then inserted into the vagina to the desired depth. After insertion, inner element 13 is pushed forward into outer element 12 as shown in FIGS. 5 and 6. Since during this operation the string 24 is held firmly against movement, the forward end of tampon 23 is also immobilized in its position on the end of shaft 15 causing the middle sections of the tampon 23 to buckle and bulge outwardly as shown at 25. This action functions primarily to break any compression set which may have occurred. As the inner element is pushed still farther forward to eject the free ends of the tampon from tube 14, the tampon is then laterally or radially spread within the vagina by the movement of the inner tube into the inside of the tampon. This increases the effective diameter of the tampon at the time of deployment to aid in blocking potential flow along the walls. Collapse of the deployed tampon inside the vagina due to differential intravaginal pressure also may cause further lateral spreading of the deployed tampon to further assist fluid blocking capabilities. When the inner element 13 is completely telescoped into outer element 12 up to stop 22, and the free ends 27 of the tampon are pushed clear of the open end of cylinder 14 and spread apart within the vagina as indicated above, it is preferred that the inner element be of sufficient length to clear the leading end of the central shaft to insure that portions of the tampon are not inadvertently trapped between the inner element and the shaft. If the latter condition occurs, withdrawal of the inserter may be hampered. However, this refinement is not essential.

Figure 1A:
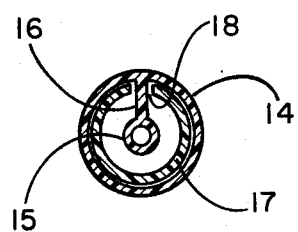
FIG. 1A is a section taken through lines 1A—1A of FIG. 1.
Figure 1B:
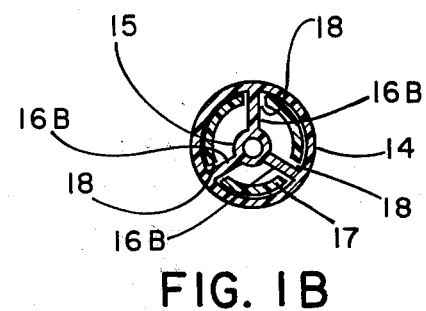
FIG. 1B is a section similar to FIG. 1A showing another embodiment.

Many variations of the basic embodiment of the inserter are possible. For example, as shown in FIG. 1B, support means for the central shaft 15 may be comprised of a multiplicity of supporting elements such as flat vanes 16b rather than a single vane 16 as shown in FIG. 1A. In such event, inner element 17 must be provided with a multiplicity of longitudinal slots 18 in order to accommodate each of the support vanes and enable slidable movement of the elements 14 and 17 with respect to each other. While a single support vane 16 is shown in FIG. 1A and three support elements such as vanes 16b are shown in FIG. 1B it is understood that the number of support elements or vanes are not critical and may be varied as desired by the manufacturer.

Figure 7:
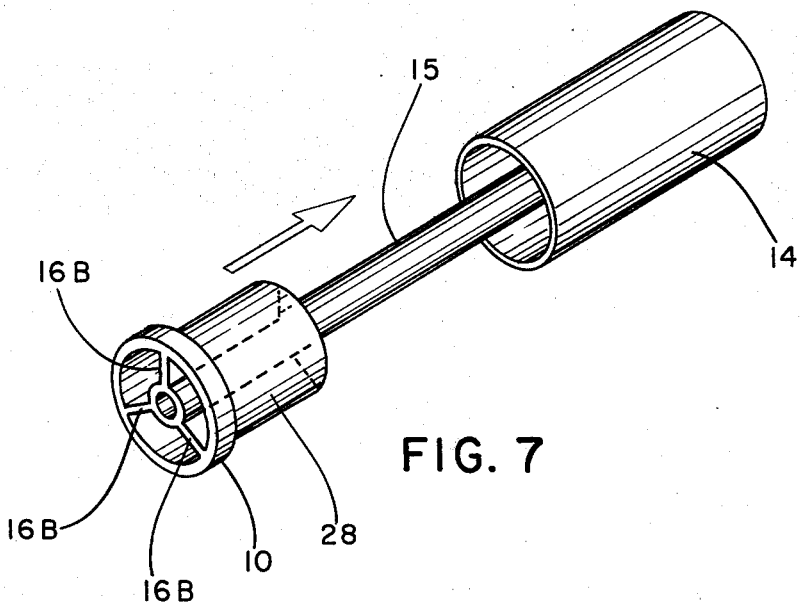
FIG. 7 is a partially exploded perspective view of another embodiment of the outer tube of the inserter showing how it may be comprised of two separate pieces.
Figure 8:
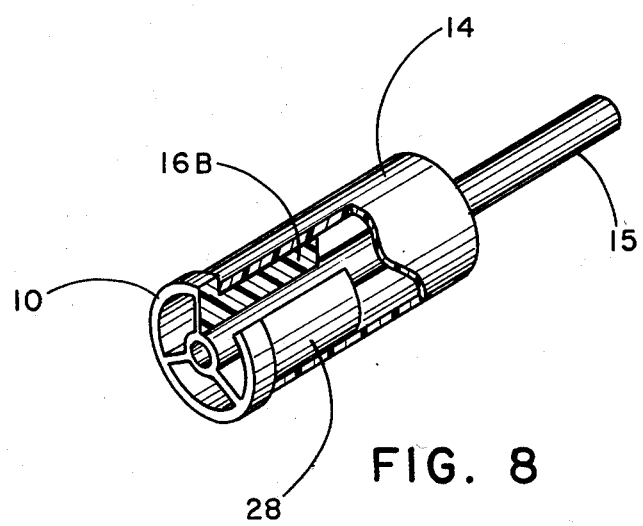
FIG. 8 is a perspective view partially cut away showing the outer tube of FIG. 7 in its assembled condition.

FIGS. 7 and 8 illustrate one embodiment of how the outer tubular element may be comprised of several members rather than being cast or molded in a single piece. In this embodiment cylinder 14 comprises one piece, while the central shaft 15, support vanes 16b and gripping ring 10 comprise a second piece along with another short cylinder 28 which is sized to snap into cylinder 14 as shown in FIG. 8. This construction permits easier assembly of the tampon-inserter combination. For example, before assembling the two pieces, the tampon may be first draped over the shaft 15 and then pushed through cylinder 14.

Figure 9:
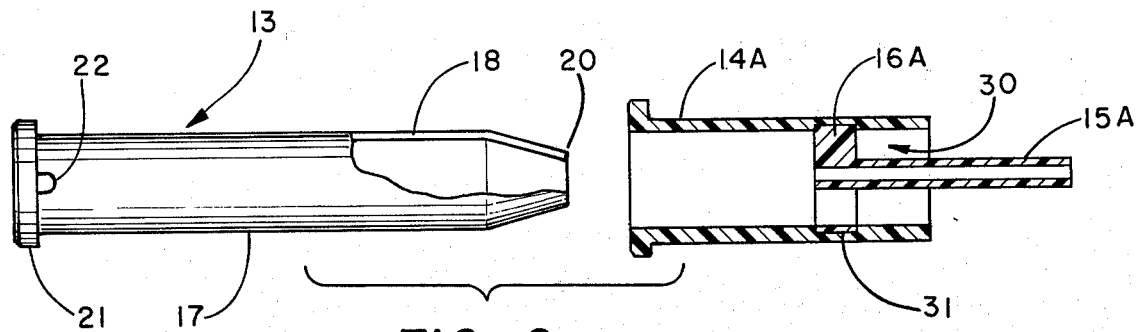
FIG. 9 is a combined partially exploded side and sectional view of another embodiment.

In FIG. 9 another variation of the outer tubular element is shown in which the central shaft 15a is suspended from a support means illustrated as vane 16a disposed near the front end of outer tube 14a. In this embodiment inner element 13 is of the same construction as shown in FIGS. 1 – 3. As indicated here, the support means for central shaft 15a may be located anywhere within outer element 14a as long as sufficient space 30 is provided at the leading end of tube 14a to accommodate the free ends of the tampon in the tampon/inserter combination. It is also understood that the central shaft and support means may also comprise a separate piece which can be snapped in place within the outer tube by suitable means. For example, by providing a circumferential groove or the like as shown at 31.

Figure 10:
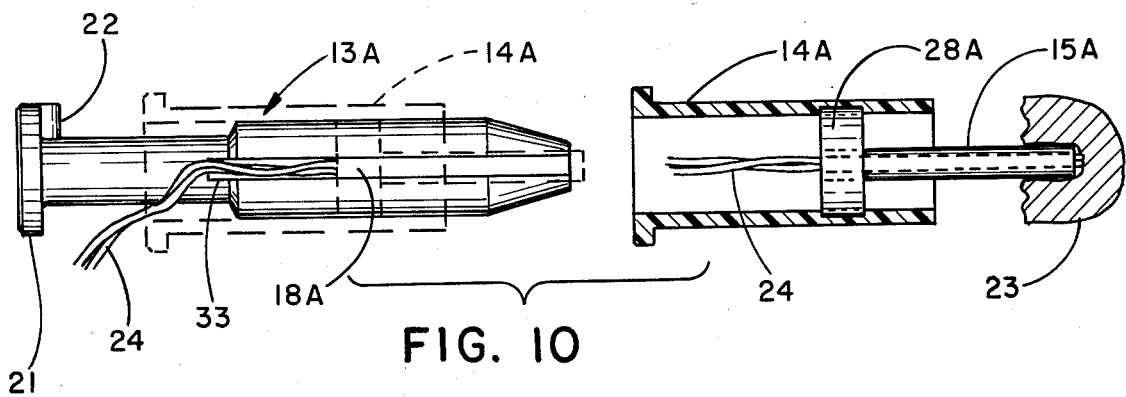
FIG. 10 is also a combined partially exploded side and sectional view of still another embodiment.

In FIG. 10, another variation is shown wherein the rear portion 32 of the inner element 13a is of smaller diameter to provide room for the withdrawal string 24 when the two elements of the inserter are telescoped together as shown by the ghost lines for outer element 14a in the left view of the figure. In the right portion of the Figure, the outer tube 14a is shown in longitudinal section, with the central shaft 15a in side view, and a portion of tampon 23 and string 24 illustrated in assembled condition. In this embodiment groove 18a in the wall of the inner element 32 may be foreshortened as at 33.

Figure 11:
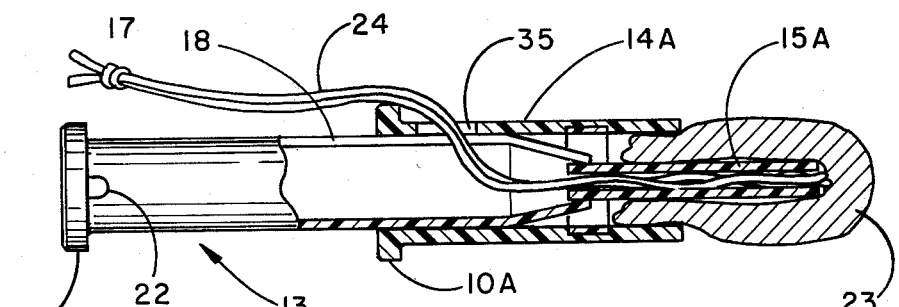
FIG. 11 is a side view, largely in longitudinal section of a further embodiment, the section being taken along lines 11—11 of FIG. 12.
Figure 12:
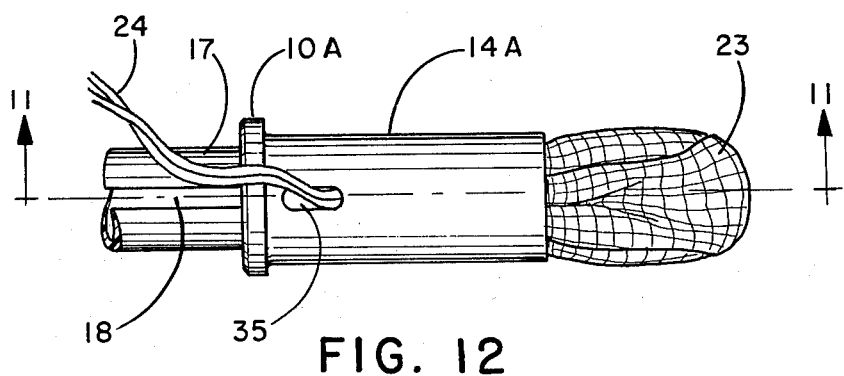
FIG. 12 is a partial plan view of the embodiment shown in FIG. 11.

FIGS. 11 and 12 show another variation and as shown is similar to the FIG. 9 embodiment. In this figure central shaft 15a is suspended from near the front end of tube 14a as in FIG. 9, but the wall of outer tube 14a is provided with an aperture 35 through which withdrawal string 24 is threaded. In this arrangement, it is much easier for the user to hold the string against movement since the string is already located outside of tube 14a adjacent ring 10a and no additional manipulation is needed to grasp it with the fingers during insertion.

The elements of this invention are preferably moulded or cast from thermoplastic materials such as polyethylene or polypropylene. Other suitable materials such as paperboard, cellulosics, water soluble polyvinyl alcohol and the like may of course be used.

Various types of tampon constructions are also adaptable for use with the inserter. The preferred tampon comprises an initially flat low density sheetlike structure which is easily draped over the central shaft of the inserter and capable of having its free ends tucked inside of the cylindrical member of the inner element. A wide variety of absorbent materials may be used including both natural and regenerated cellulosic fibers, hydrophilic sponges of various types such as polyurethanes and the like, and various combinations of these materials.

While the primary advantage of this inserter is the ability to deliver and then radially and laterally spread a soft conformable tampon within the vagina, it can also be used to merely deliver the tampon with a somewhat lesser degree of lateral spreading. This is done by telescoping the elements together without first holding the string immobilized.

In the preferred embodiment, the front end 19 of the inner tubular element 17 is shown as being tapered. This taper may be conical or it may be chisel-like, i.e. a flat-sided wedge. While the tapered configuration is preferred, the inner element may also be blunt-nosed, but the latter is less desirable since very little radial or lateral spreading occurs. In such event, however, the blunt-nosed inner element should also have a small diameter opening at its leading end where it is in contact with the central shaft of the outer element in order to embrace, slidably engage, and be guided along the shaft.

What is claimed is:

1. A tampon inserter comprising an outer tubular member and an inner tubular member in telescopic association; said outer tubular member being open-ended, being provided with a leading end and trailing end, and having an elongated central shaft axially disposed on the interior of said outer tubular member; said central shaft being held in its axial disposition within said outer tubular member by support means disposed in association with the interior of said outer tubular member; and said central shaft extending from said interior through a portion of said outer tubular member beyond the leading end of said outer tubular member for a predetermined distance; said inner tubular member being longer than said outer tubular member and having a forward end slidably positioned inside the trailing end of said outer tubular member; a front portion of the forward end of said inner tubular member being of reduced diameter to encircle and embrace said central shaft in slidable engagement therewith; the wall of said inner tubular member being provided with at least one longitudinal slot to accommodate said shaft support means and to permit longitudinal slidable movement of said inner tubular member within said outer tubular member from a first position wherein said forward end portion of said inner tubular member is disposed within said trailing end of said outer tubular member to a second position wherein said forward end portion of said inner tubular member is disposed beyond said leading end of said outer tubular member.

2. The tampon inserter of claim 1 wherein a rear portion of said inner tubular element is of reduced diameter.

3. The tampon inserter of claim 1 wherein the wall of said outer element adjacent the trailing end of said element is provided with an aperture through which a tampon withdrawal string may be threaded.

4. The tampon inserter of claim 1 wherein said central shaft is a hollow tube.

5. The tampon inserter of claim 1 wherein said support means is in the form of a single narrow flat vane extending from the inner wall of the outer tubular member to said shaft.

6. The tampon inserter of claim 1 wherein said support means comprises a multiplicity of spaced elements extending from the inner wall of the outer tubular member to said shaft.

7. The tampon inserter of claim 6 wherein said inner tubular member is provided with a multiplicity of longitudinal slots to accommodate said spaced elements.

8. The tampon inserter of claim 1 wherein the front portion of the forward end of said inner tubular member is tapered.

9. The tampon inserter of claim 8 wherein said tapered front portion is conical.

10. The tampon inserter of claim 8 wherein said tapered front portion is chisel-shaped.

11. The tampon inserter of claim 1 wherein said shaft and said support means comprise a piece separate from said outer tubular member, said support means comprising a ring having at least one vane extending from its inner wall to said shaft, said ring being adapted to snap inside of said outer tubular member.

12. The tampon inserter of claim 11 wherein said ring is provided with a plurality of spaced vanes to support said shaft.

13. The tampon inserter of claim 11 wherein said separate piece is disposed near the trailing end of said outer tubular member.

14. The tampon inserter of claim 13 wherein said separate piece is disposed near the leading end of said outer tubular member.

* * * * *